(12) United States Patent
Firstenberg et al.

(10) Patent No.: US 9,464,968 B2
(45) Date of Patent: Oct. 11, 2016

(54) MOBILE SAMPLE COLLECTION SYSTEM

(71) Applicant: TIERRA SOLUTIONS, INC., East Brunswick, NJ (US)

(72) Inventors: Clifford E. Firstenberg, Williamsburg, VA (US); Alain P. Hebert, Cranbury, NJ (US); Diane L. Waldschmidt, Allison Park, PA (US)

(73) Assignee: Tierra Solutions, Inc., East Brunswick, NJ (US)

( * ) Notice: Subject to any disclaimer, the term of this patent is extended or adjusted under 35 U.S.C. 154(b) by 332 days.

(21) Appl. No.: 14/083,955

(22) Filed: Nov. 19, 2013

(65) Prior Publication Data

US 2015/0135807 A1    May 21, 2015

(51) Int. Cl.
*G01N 1/14* (2006.01)
*G01N 33/18* (2006.01)
*G01N 1/40* (2006.01)

(52) U.S. Cl.
CPC ............. *G01N 1/14* (2013.01); *G01N 33/18* (2013.01); *G01N 1/4077* (2013.01); *Y10T 29/4924* (2015.01)

(58) Field of Classification Search
CPC ...... G01N 1/14; G01N 1/4077; G01N 33/18; G01N 33/1826; G01N 33/1833
USPC ......... 73/61.59, 61.71, 61.72, 64.56, 863.21, 73/863.83, 864.34
See application file for complete search history.

(56) References Cited

U.S. PATENT DOCUMENTS 4,055,986 A * 11/1977 Stewart .............. G01N 33/2823
                                                73/61.43
4,207,450 A *  6/1980 Mittleman ......... G01N 33/1833
                                                250/301
4,210,015 A *  7/1980 Euzen ................ G01N 33/2823
                                                73/61.43

(Continued)

FOREIGN PATENT DOCUMENTS

DE          3831549 C1    3/1990
DE      102005061415 A1   6/2007

OTHER PUBLICATIONS

Erosion and Sediment Transport Monitoring Programmes in River Basins (Proceedings of the Oslo Symposium, Aug. 1992), IAH Publ. No. 210, 1992; Environmental quality: changing times for sediment programs; E.D. Ongley, National Water Research Institute, Canada Center for Inland Waters, P.O. Box 5050, Burlington, Ontario, Canada L7R 4A6.

*Primary Examiner* — Daniel S Larkin
(74) *Attorney, Agent, or Firm* — Sean S. Wooden; Andrews Kurth LLP

(57) ABSTRACT

A mobile sample collection system including housing enclosing a main influent peristaltic pump operatively connected to the main tubing line; a continuous flow centrifuge (CFC) operatively connected to the main tubing line, the CFC comprising a centrifuge bowl; and an elutriate collection tank receiving elutriate from the CFC. The main influent peristaltic pump is configured to continuously pump fluids from a liquid source through the main tubing line and into the CFC. The fluids, containing suspended solids and dissolved solids, are processed through the CFC so that the suspended solids are retained on the centrifuge bowl and the dissolved solids are pumped out of the CFC through the main tubing line and into the elutriate collection tank for sample collection and analysis. The elutriate collection tank includes a tank liner configured to prevent direct contact of pumped fluids with the tank. Excess fluids are returned to the liquid source.

13 Claims, 3 Drawing Sheets

(56) References Cited

U.S. PATENT DOCUMENTS

| | | | |
|---|---|---|---|
| 4,252,020 A | 2/1981 | Ongley | |
| 4,510,060 A * | 4/1985 | Stewart | G01N 33/2823 134/22.11 |
| 4,628,748 A * | 12/1986 | Jogan | G01N 1/10 73/863.01 |
| 4,660,607 A * | 4/1987 | Griffith | F04B 49/10 141/1 |
| 4,818,348 A | 4/1989 | Stetter | |
| 5,167,802 A * | 12/1992 | Sandstrom | G01N 1/18 137/565.3 |
| 5,197,340 A | 3/1993 | Jones | |
| 5,211,203 A | 5/1993 | Vollweiler et al. | |
| 5,441,071 A | 8/1995 | Doherty et al. | |
| 5,711,916 A | 1/1998 | Riggs et al. | |
| 6,182,503 B1 * | 2/2001 | Mode | G01N 11/08 137/110 |
| 6,338,282 B1 | 1/2002 | Gilbert | |
| 6,662,632 B1 * | 12/2003 | Parker | G01M 3/186 340/604 |
| 7,985,382 B1 | 7/2011 | Henry et al. | |
| 2004/0244965 A1 | 12/2004 | Face | |
| 2005/0116299 A1 * | 6/2005 | Koning | H05K 3/005 257/374 |
| 2006/0016728 A1 | 1/2006 | Shorts | |
| 2008/0022787 A1 | 1/2008 | Herzog | |
| 2009/0187356 A1 | 7/2009 | Artiuch | |
| 2011/0084028 A1 | 4/2011 | Stanfel et al. | |
| 2012/0258523 A1 | 10/2012 | Summer et al. | |

* cited by examiner

MOBILE SAMPLE COLLECTION SYSTEM

FIELD

This application relates generally to monitoring and testing of liquid samples. More particularly, this application relates to a sample collection system for water quality monitoring and trace contaminant detection and quantitation.

BACKGROUND

Stormwater runoff is rain that falls on streets, parking areas, sports fields, gravel lots, rooftops or other developed land and flows directly into nearby lakes, rivers and other water landforms. The drizzling or pounding rain picks up and mixes with contaminants on the ground, such as oil, grease, metals and coolants from vehicles; fertilizers, pesticides and other chemicals from gardens and homes; bacteria from pet wastes and failing septic systems; soil from construction sites and other bare ground; soaps from car or equipment washing; and accidental spills, leaky storage containers, and whatever else ends up on the ground. The polluted runoff then rushes into nearby gutters and storm drains and into streams, lakes, rivers, and bays. In most areas, stormwater runoff enters these receiving water bodies without being cleaned of pollutants.

Increasingly, government entities are instituting strict regulations for the management of stormwater and industrial runoff. Despite increasing public concern surrounding this issue, the current infrastructure does not adequately control the release of contaminated stormwater or combined sanitary sewage and stormwater to receiving water bodies. Stormwater and industrial runoff can be contaminated with a highly variable mix of particulate-bound and dissolved contaminants. Due to the large volume of water discharged into water bodies during runoff events, even small quantities of contaminants can have a significant environmental impact.

It is desirable to be able to collect combined sewer and stormwater effluent samples for laboratory analysis to facilitate an accurate characterization of contaminants in water discharged into bodies of water. These contaminants are typically bound to particulates and, to a lesser degree, in the dissolved phase. Quantitation limits associated with the particulate-phase of the effluent are particularly challenging to achieve, in that the low target quantitation limits require a sufficiently large mass of solids to be collected for detection via standard, approved laboratory analytical methods. To obtain the required mass of solids, it is essential that a sufficient volume of effluent be collected in the field.

To determine contaminant load in water, it is necessary to analyze, separately, the dissolved and solids matrices (or fractions). Traditionally, the solids fraction is obtained by forcing water through a filter, whereby trapped solids are sent to a laboratory for chemical analysis. To ensure that all of the trapped solids are accounted for in the analysis, the whole filter is processed (i.e., it would be impossible to volumetrically separate the trapped solids from the filter). Consequently, the filter must not have any trace contaminants present as artifacts that can contribute to the analytical results obtained (which would produce a biased result). This process has several additional limitations, including the ability to only trap small masses of particulates, which precludes detection of many chemicals at trace concentrations, and which necessarily requires many filters, possibly hundreds when multiple analyses are necessary to characterize the range of contaminants of interest. This methodology further suffers from a lack of efficiency and poor quality control due to the many potential sources of error or contamination, including the moisture retained in the filters that adversely affects the analytical method.

U.S. Pat. No. 4,252,020 to Ongley describes a method and apparatus for the quantitative recovery of solids suspended in a fluid involving the use of a continuous flow centrifugation sampling apparatus. Although this system represents an improvement over the filter processing method above, it does not provide a sufficient "clean room" environment to facilitate accurate trace contaminant detection, nor does it have a sufficiently high processing capacity. Consequently, accuracy and trace contaminant detection is reduced.

In view of the above-described problems and limitations, there is a need for improved sample collection systems for water quality monitoring. The present invention overcomes the above-described problems and limitations by providing an efficient, high capacity, high throughput sample collection system in a clean room environment so as to provide increased accuracy, sensitivity and characterization of contaminants in large volume water sampling investigations.

SUMMARY

In one aspect, a mobile sample collection system includes a housing enclosing a main influent peristaltic pump operatively connected to a main tubing line; a continuous flow centrifuge (CFC) operatively connected to the main tubing line, the CFC comprising a centrifuge bowl; and an elutriate collection tank receiving elutriate from the CFC. The main influent peristaltic pump is configured to continuously pump fluids from a liquid source through the main tubing line and into the CFC. The fluids, containing suspended solids and dissolved solids, are processed through the CFC so that the suspended solids are retained on the centrifuge bowl and so that the dissolved solids are pumped out of the CFC through the main tubing line and into the elutriate collection tank for sample collection and analysis. The elutriate collection tank includes a tank liner configured to prevent direct contact of pumped fluids with the tank. Excess fluids are returned to the water source. In preferred embodiments, the housing includes a climate-controlled trailer.

Other system features include one or more sampling ports connectively linking the main tubing line to one or more peristaltic sampling pumps. For example, in one embodiment the system includes a first sampling port connectively linking the main tubing line to a secondary tubing line operatively linked to a first peristaltic sampling pump configured to pump fluid containing dissolved solids from the CFC into the elutriate collection tank for sample collection and analysis. In another embodiment, the system includes a second sampling port connectively linking the main tubing line to a secondary tubing line operatively linked to a second sampling pump configured to pump the fluids containing suspended and dissolved solids from the liquid source into a bulk liquid collection tank for sample collection and analysis. In yet another embodiment, the system includes a third sampling port connectively linking the main tubing line to a secondary tubing line operatively linked to a third sampling pump configured to pump the fluids from the liquid source as samples for direct analysis and real-time quality monitoring. In each scenario above the secondary pumps may be preset to collect time-weighted subsamples in the tanks over the anticipated duration of sample collection. In a preferred embodiment, the system includes a combination of all three sampling ports, their associated secondary tubing and secondary sampling pumps.

In another aspect, a method for assembling the above described mobile sample collection system provides a main influent peristaltic pump, a main tubing line and a CFC; operatively configures the main influent peristaltic pump to continuously pump fluids from a liquid source through the main tubing line, into the CFC and back to the liquid source; and operatively connects the elutriate collection tank so as to enable fluid containing dissolved solids to exit from the CFC through the main tubing line for collection in the elutriate collection tank.

In a further aspect, a method for determining the concentration of a contaminant in a liquid sample provides a mobile sample collection system as described herein; pumps fluids from a liquid source through the main tubing line and into the CFC; processes the fluids through the CFC; collects a sample containing solid materials processed through the CFC; and the concentration of the contaminants in the sample can be determined.

In one embodiment, the sample contains suspended solids, whereby the contaminant is adsorbed to a solid. In another embodiment, the sample contains the contaminant adsorbed to a solid retained on the centrifuge bowl. In another embodiment, the sample contains dissolved solids exiting from the CFC, whereby the contaminant is present as a dissolved solid.

DETAILED DESCRIPTION

Figure 1:
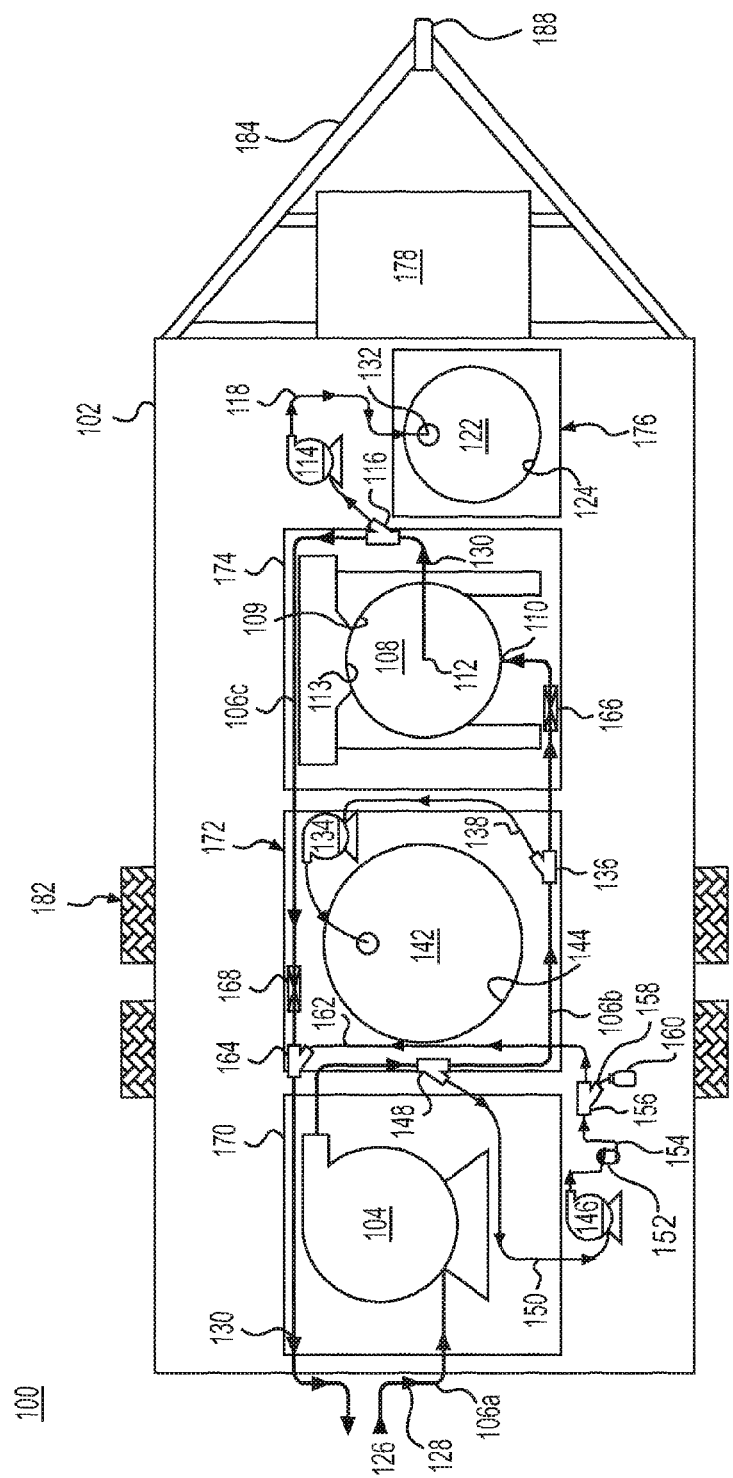
FIG. 1 is a schematic depiction of an exemplary mobile sample collection system embodying principles of the invention in accordance with one embodiment of the invention.

FIG. 1 depicts an exemplary mobile sample collection system 100 according to one embodiment of the present invention. The mobile sample collection system 100 includes housing 102 enclosing a main influent pump 104 operatively connected to a main tubing line 106a, b, c. The system 100 further includes a continuous flow centrifuge (CFC) 108 containing a large volume centrifuge bowl 109. The CFC 108 includes a CFC inlet 110 and a CFC outlet 112, each CFC inlet 110 and CFC outlet 112 being operatively connected to the main tubing line 106b, 106c, respectively.

The system 100 further includes a first sampling pump 114 operatively connected to an elutriate collection tank 122. The elutriate collection tank 122 includes a tank liner 124. The main influent pump 104 is configured to continuously pump fluids 128 from a liquid source 126 (such as water) through the main tubing line 106a and into the CFC 108, processing the fluids 128 so that suspended solids are retained in the centrifuge bowl 109 on a centrifuge bowl liner 113 and so that dissolved solids are collected as fluids 130 pumped from the CFC 108 into the elutriate collection tank 122, whereby fluids 130 are pumped through a first sampling port 116 connectively linking the main tubing lines 106a, 106b to a secondary tubing line 116 operatively linked to a first peristaltic pump 114 pumping a portion of the dissolved fluids into the elutriate collection tank 122 for sample analysis. Another portion of the fluids 130 is pumped out from the CFC 108 and returned to the liquid source 126. The main tubing lines 106a, 106b, 106c collectively includes tubing 106a connectively linking the liquid source 126 to the main influent pump 104, tubing 106b connectively linking the main influent pump 104 to the CFC 108, and tubing 106c connectively linking the CFC 108 back to the liquid source 126.

Figure 2:
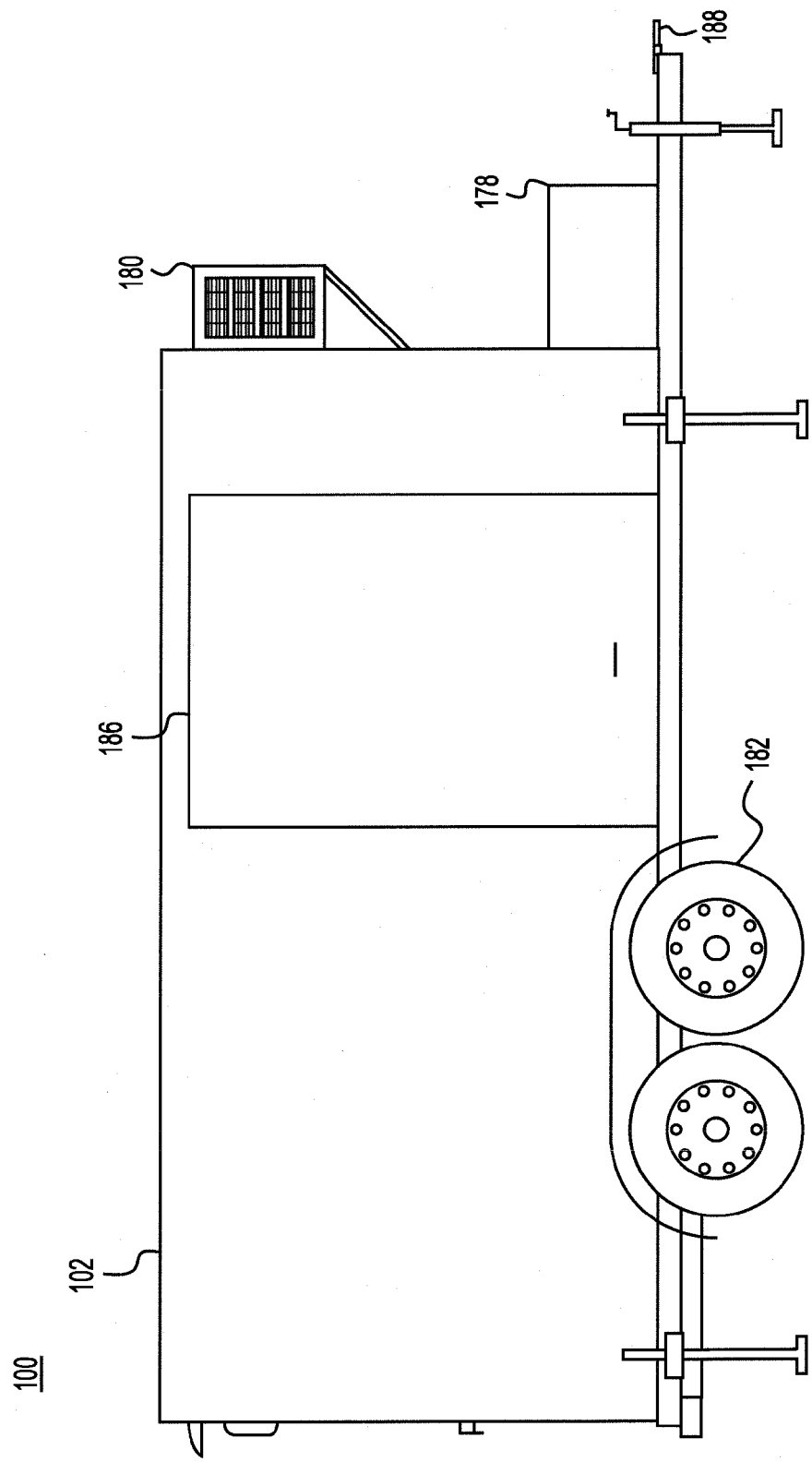
FIG. 2 is a side view of the mobile sample collection system depicted in FIG. 1.

The housing includes a mobile trailer 102 as depicted in FIG. 2. Preferably, the housing includes a climate-controlled trailer 102. In certain embodiments, the climate-controlled trailer 102 can be refrigerated. A mobile trailer 102 may include a side door 186 and can provide a secure platform for housing and/or mounting the sample collection system 100 and associated components.

The main influent pump 104 is used for pumping a suitable amount of fluids 128 from a selected liquid source 126 at a suitable flow rate to facilitate a sufficient mass of solids collection. The sample collection system 100 may pump fluids up to, for example, 2,000 gallons (or more) of liquid at a minimum flow rate of at least 5 gallons per minute (gpm), preferably at least 10 gpm, more preferably at least 15 gpm through the sample collection system 100. However, depending on the nature and possible concentration range(s) of the target analyte(s) or contaminant(s) for evaluation, the sample collection system 100 may, in principle, pump virtually any selected volume of fluid from the selected liquid source.

The liquid sample collection system and methods described herein are applicable for use in a variety of sites desirable for water testing, including, but not limited to sites of stormwater runoff, such as stormwater outfall (SWO) and combined sewer overflow (SWO) sites, as well as groundwater sources, lakes, rivers, and oceans. Water sources for testing may be accessed through, for example, a manhole, regulator chamber, natural body of water directly, etc. It should be understood that the liquid sampling system may be utilized for any application in which monitoring, testing and quantitation of dissolved and/or suspended solids or contaminants in fluid samples is desired.

The sample collection process can be extremely sensitive to any potential contamination within the system. Accordingly, the sample collection equipment is preferably selected based on the materials and their ability to minimize/eliminate potential contamination of samples from the sampling equipment. By way of example, it is important that the main influent pump 104 and any secondary sampling pumps be chosen to exclude moving parts in direct contact with the fluid being pumped. Accordingly, in preferred embodiments, the main influent pump 104 and the secondary sampling pumps utilize peristaltic pumps, since they do not have moving parts in direct contact with the fluid being pumped. The main influent pump 104 may be a rotary peristaltic pump or a linear peristaltic pump.

Sample ports, sample tubing and secondary pumps may be operatively connected to the main tubing lines 106a, 106b, 106c to pump fluids 128 from the main tubing lines 106a, 106b, 106c into bulk sample collection tanks and/or through e.g., a water quality meter and into a sample bottle. Small-diameter sample tubing and smaller, preferably peristaltic pumps (e.g., pumps 114, 134, 146 with flow rates up to 1 gpm) may be connected to the sample ports. The smaller pumps may be installed along with corresponding sample ports in the process system for easy connect and disconnect. Preferably, the sampling pumps will not have moving parts that will come in direct contact with the fluid being pumped due to the potential for sample contamination. Accordingly, peristaltic pumps are a preferred pump type for this operation.

FIG. 1 illustrates an embodiment containing two ports before 136, 148 and one port 116 after the CFC 108. In FIG. 1, a first sampling pump 114 pumps fluids exiting from the CFC 108 via a first port 116 and a first sample tubing 118 into an elutriate collection tank 122 (e.g., 65 gallon tank) to store fluids for aqueous sampling and subsequent laboratory analysis. A second sampling pump 134 pumps effluent fluids 128 from the liquid source 126 via a second port 136 and a second sample tubing 138 into a bulk liquid collection tank 142 (e.g., 125 gallon tank) to store fluids for aqueous sampling and subsequent laboratory analysis. Each of the tanks contains a liner 124 and 144 made of Teflon or equivalent material to prevent direct contact of pumped fluids 128 with the sample collection tank 122 as further described below. A third sampling pump 146 pumps fluids 128 from the liquid source 126 via a third sample port 148 and a third sample tubing 150 into e.g., a water quality monitor 152 for real-time water quality monitoring. A fourth port 116 links sample tubing 154 from the water quality monitor 152 to a fifth port 164 via sample tubing 162 for entry into the main tubing line 106c and to a sample bottle 160 via sample tubing 158 for collecting discrete samples that can be analyzed to determine total suspended solids (TSS) and total dissolved solids (TDS) concentrations in the fluids prior to separation/processing. These samples may be collected at pre-determined time intervals which can allow for characterization of TSS and TDS in the incoming liquid throughout the duration of a sample collection process. As shown in FIG. 1, the sample collection system 100 may further include one or more flow meters 166, 168 installed in-line with the main tubing lines 106a, 106b, 106c. In FIG. 1, a first flow meter 166 is positioned before the CFC 108 and a second flow meter 168 is positioned following the first sample port 156. Following the CFC 108, the remainder of the main tubing line 106c may return the processed fluid products 130 to the liquid source 126 via a manhole, regulator chamber, etc.

The main influent pump 104 will typically contain a variable speed motor of at least 1 hp, preferably 2 hp, 120/240-volt and may accept single continuous flexible inert tubing having a hose diameter between 0.5-1 inch. Preferably the main influent pump 104 has a vertical (suction) head of at least 25 feet and a pressure at discharge of at least 15 pounds per square inch (psi) or a pressure at discharge that meets the CFC injection requirements. The main influent peristaltic pump may be mounted on a mobile skid 170 for easy installation and lockdown in the trailer 102 and removal from the trailer 102.

An exemplary main influent peristaltic pump 104 for use in the present invention may be obtained from Watson-Marlow Bredel and include the SPX25 and SPX32 peristaltic pumps. The SPX 32 pump is a rotary peristaltic pump which uses positive displacement to move material. The fluids enter the pump through tubing, which may be circular or arched in shape. A rotor fitted with "rollers" rolls over the tubing, compressing it and pushing the material through the pump, and out an exit nozzle.

Secondary sampling pumps 114, 134, 146 will typically have a variable flow rate up to about 1 gpm and may contain a variable speed motor of at least 0.5 hp, 120-volt and may accept single continuous flexible inert tubing having a typical hose diameter of about 0.5 inches (outside diameter [OD]). Exemplary sampling pumps for use in the present invention may be obtained from Watson-Marlow Bredel and include the SPX 15 peristaltic pumps.

Tubing materials are preferably constructed from inert, non-leaching materials (i.e., Teflon®-lined or equivalent). Generally, the tubing should be flexible, structurally capable, and manufacturer-approved to withstand forces imposed on the tubing from e.g., the rollers within the peristaltic pumps.

The main tubing lines 106a, 106b, 106c in the sample collection system 100 may utilize tubing having a diameter of at least 1.0 inch OD, preferably an OD of least 1.25 inches, more preferably an OD of about 1.5 inches. The sample tubing lines 118, 138, 150 may utilize tubing having a diameter of at least 0.25 inch OD, more preferably an OD of about 0.5 inches.

Fluid 128 is pumped through the main tubing lines 106a, 106b to the CFC 108, where suspended solids are separated from dissolved solids 132 such that the suspended solids are retained on the CFC bowl 109 for further sample analysis. The dissolved solids 132 (or total dissolved solids (TDS)) are not retained on the CFC bowl 109 and are pumped out of the CFC 108 and collected for further sample analysis. In particular, sampling pump 114 is configured to pump total dissolved solids (TDS) exiting from the CFC 108 into the elutriate collection tank 122. The suspended solids accumulating in the CFC bowl 109 are retrieved at the end of the sampling event by opening the CFC bowl 109 and removing the solids retained thereon. The bowl 109 is preferably made of stainless steel, such as grade SX 316/316L or equivalent, and is preferably lined with a Teflon or equivalent inert liner to aid in the removal and evaluation of recovered solids therefrom.

Preferably, the CFC is a single-bowl centrifuge or equivalent capable of generating a centrifugal force of at least 10,000 g, more preferably at least 13,000 g. The CFC may allow for a minimum flow rate of at least 5 gpm, preferably at least 10 gpm, more preferably at least 15 gpm, and/or up to about 25 gpm or 40 gpm and may have a variable frequency drive for speed control. A 5 hp, 3-phase, 60 cycle motor may be suitable for driving the CFC. The CFC motor (not shown) can be adapted with a single-phase to three-phase converter from the supplier. Exemplary CFCs for use in the present invention include the Sharples Super Centrifuge (Model # AS-26 model) and the Pennwalt High-G Tubular Bowl Super Centrifuge.

Preferably, the fittings and valves for the CFC 108 are constructed of material able to minimize/eliminate potential contamination of samples from the sampling equipment as further described below. The CFC 108 may be equipped with an isolation pad and leveling jacks affixed to the trailer 102. The CFC 108 may be mounted on a mobile skid 174 for easy installation and lockdown in the trailer 102 and removal from the trailer 102.

Flow meters 166, 168 or totalizers may be used to measure flow rate and total flow in the system 100. Flow meters/totalizers may be installed around the outside wall of the main tubing lines 106a, 106b, 106c so as to eliminate contact with the pumped fluids 128, 130 and the potential for equipment cross-contamination. An exemplary flow meter/totalizer for use in the present invention is a magnetic meter/totalizer from Endress-Hauser, Inc., such as the Promag 53 H magnetic flow meter.

A water quality meter 152 may be used to perform real-time monitoring during sample collection as part of the sample collection system. An in-line water quality meter 152 may be installed along the third sampling port 148 to conduct real-time monitoring of the pumped fluid 128. An exemplary water quality meter 152 for use in the present invention may be obtained from YSI, Inc. and includes the 600XLM V2 model with flow-through cell.

Valves and fittings can be used to assemble and install the various components of the sample collection system 100. Valves and fittings may be, for example, 1.5 inches and 0.5 inches for the tubing components and other sizes suitably adapted to the various equipment connections. Valves and fittings used for construction of the sample collection system mechanical components preferably utilize inert materials (Teflon®-lined, stainless steel (SX 316/316L), etc.), rather than compounds or chemicals that may have the potential to leach contaminants into the pumped fluid samples.

Sample tubing material is preferably made from an inert, non-leaching material (e.g., Teflon® or equivalent). Teflon® tubing has been widely used for environmental sample collection as it is an inert/non-leaching material. Tubing should also be flexible and structurally capable to withstand forces imposed on the tubing from the rollers within the specified peristaltic pumps.

Bulk sample collection tanks 122, 142 may be used to store pumped fluids for sampling purposes. The tanks may be constructed of polyethylene and may be sized and selected appropriately to handle liquid volumes to be collected during sampling (e.g., 65 and 125 gallons) and preferably include removable lids. An exemplary tank supplier is Chem-Tainer Industries, Inc. The bulk sample collection tanks 122, 142 may be mounted on mobile skids 176, 172, respectively, for easy installation and lockdown in the trailer 102 and removal from the trailer 102.

The bulk sample collection tanks 122, 142 are fitted with tank liners (Teflon® or equivalent) in order to avoid direct contact of the pumped fluid with the tanks and to eliminate potential cross-contamination and the need for decontamination between sampling events. The liners can be of standard size and volume, based on the size of the collection tanks and may be obtained from any suitable supplier, such as DuPont.

In certain embodiments, the sample collection tanks are insulated (e.g., double-walled) and hold ice to facilitate chilling of the liquids during collection. In addition, the collection tanks may be fitted with stirrers, preferably made from inert materials, to keep the liquid samples homogenized.

The mobile sample collection system 100 may include appropriate electrical system components, a generator 178 to provide power for the sample collection system (e.g., CFC, peristaltic pumps), work lighting, and other miscellaneous equipment (e.g., power tools, laptops). As depicted in FIGS. 1 and 2, the generator 178 may be installed on the A-frame 184 of the trailer 102 including dual axle wheels 182. An exemplary generator 178 for use in the present invention is a 15,000 watt rated (22,500 surge watts) 3-phase 120/240 volt propane (or diesel) generator driven by a 30 hp motor. In certain embodiments the generator may be spaced from the trailer to reduce the possibility of exhaust fumes entering the trailer, preferably at a location downwind from the trailer.

Breaker (power) panel and electrical components, including breakers, switches, six outlets, overhead indoor lighting, outdoor trailer-mounted flood lights, and associated wiring and conduit can be included for operation of the sample collection system 100 as appropriate.

A tow-behind trailer 102 may be used to house the sample collection system 100 and associated components. The trailer 102 is preferably configured as an enclosed climate-controlled unit. As such, the trailer may be insulated and refrigerated. In one particular embodiment, an insulated and refrigerated sample collection trailer 102 is about 16 feet in length×8 feet in width×8 feet in height housing the sample collection system 100. The trailer floor may be skid-resistant and equipped with a tie-down lockdown system. The sample collection system 100 and associated components may be fastened to movable skids 170, 172, 174, 176 secured to the floor of the trailer 102.

In one embodiment, the trailer 102 contains a refrigeration unit 180 capable of maintaining a temperature of 40° F. (e.g., 12,000 BTU air conditioning unit with 5 hp compressor) for samples inside the trailer 102 during the summer and a thermostat for temperature control. The trailer 102 will typically have roll-up rear access, a roll-up equipment door on each side, a pintle hook trailer hitch connection 188, a standard 7 pin trailer wiring connection.

Figure 3:
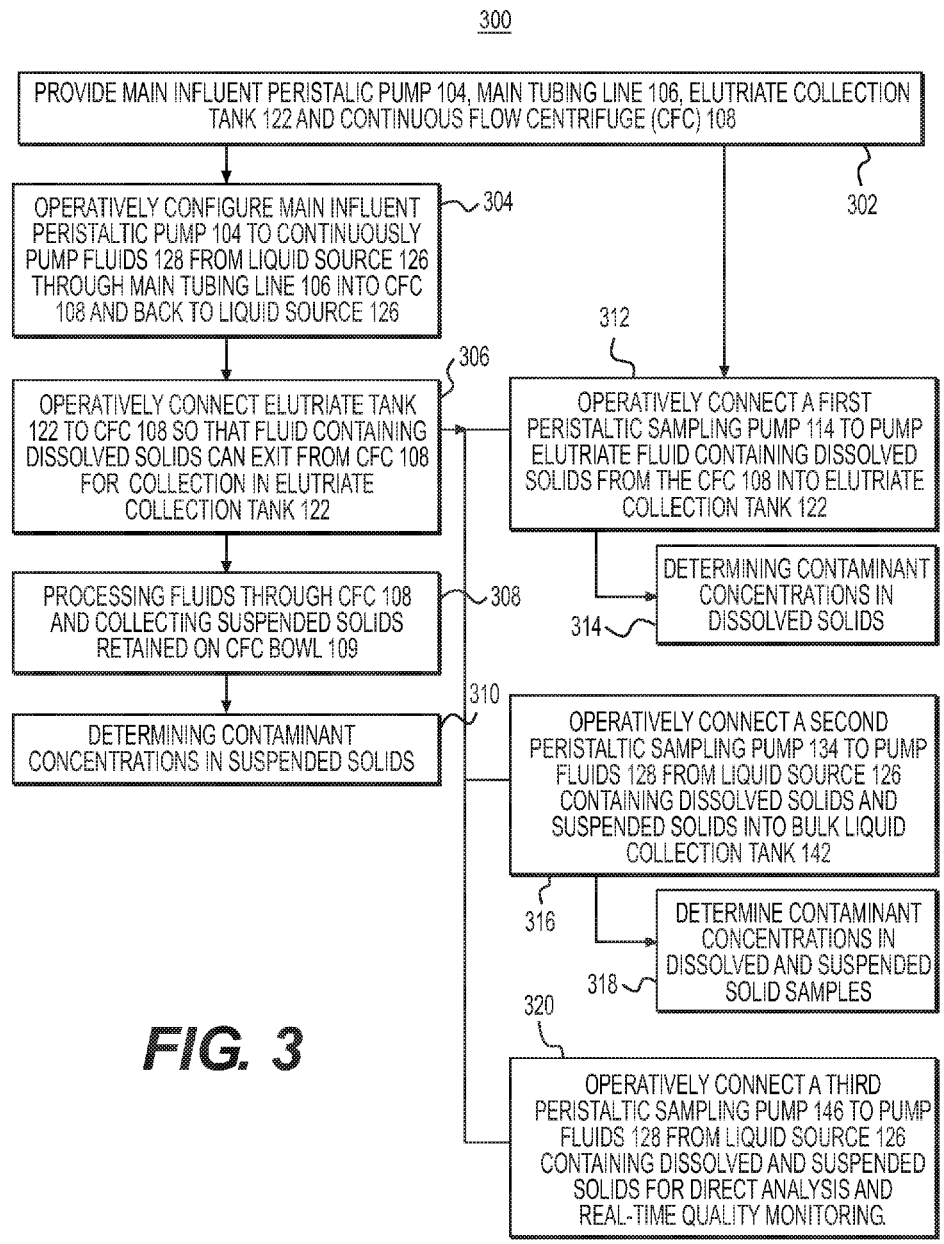
FIG. 3 is a flow diagram illustrating an exemplary method for assembling and using the mobile sample collection system.

In another aspect depicted in FIG. 3, a method 300 for assembling a mobile sample collection system 100 provides a main influent peristaltic pump 104, a main tubing lines 106a, 106b, 106c, an elutriate collection tank 122 and a CFC 108 (302); operatively configures the main influent peristaltic pump 104 to continuously pump fluids 128 from a liquid source 126 through the main tubing lines 106a, 106b, 106c, into the CFC 108 and back into the liquid source 126 (304), and operatively connects the elutriate collection tank 122 to the CFC 108 so as to enable fluid containing dissolved solids to exit from the CFC 108 through the main tubing line 106c for collection in the elutriate collection tank 122 (306). Suspended solids from the liquid source (126) processed through the CFC 108 are retained in the CFC bowl 109 (308) and retrieved after completion of the sampling event for determining contaminant concentrations in the suspended solids (310).

In one embodiment, a first sampling port 116 is connectively linked between the main tubing line 106b and a secondary tubing line 118. The secondary tubing line 118 is operatively linked to a first peristaltic sampling pump 114 configured to pump elutriate fluid comprising dissolved solids from the CFC 108 into the elutriate collection tank 122 (312) for determining contaminant concentrations of dissolved solids in the liquid sample (314).

A second sampling port 136 may be connectively linked between the main tubing line 106b and a secondary tubing line 138 operatively linked to a second peristaltic sampling pump 134 configured to pump the fluids comprising suspended solids and dissolved solids from the liquid source 126 into a bulk liquid collection tank 142 (316) for determining contaminant concentrations in dissolved and suspended solid samples (318). A third sampling port 148 may be connectively linked between the main tubing line 106a and a secondary tubing line 150 operatively linked to a third peristaltic sampling pump 146 configured to pump the fluids from the liquid source 126 as samples for direct analysis and real-time water quality monitoring (320).

In a further aspect, a method for determining the concentration of a contaminant in a liquid sample includes: providing a sample collection system 100 as described above; pumping fluids from a liquid source through the main tubing line and into the CFC; processing the fluids through the CFC; collecting a sample comprising solid materials processed through the CFC; and determining the concentration of the contaminant in the sample.

In one embodiment, the sample contains suspended solids and the contaminant is adsorbed to a solid. In another embodiment, the sample contains a contaminant adsorbed to a solid retained on the centrifuge bowl 109. In another embodiment, the sample contains dissolved solids exiting from the CFC 108 and the contaminant is present as a dissolved solid.

Exemplary contaminants for detection include, but are not limited to, polychlorinated dibenzo-p-dioxins/polychlorinated dibenzofurans (PCDDs/PCDFs), polychlorinated biphenyl (PCB) congeners, aroclor PCBs, organochlorine pesticides, semivolatile organic compounds (SVOCs), semivolatile organics determined using selective ion monitoring (SVOC SIM), chlorinated herbicides, cyanide, volatile organic compounds (VOCs), total extractable petroleum hydrocarbon (TEPH), total organic carbon (TOC) and the like.

The sample collection system 100 described herein is capable of sample collection such that trace contaminants in liquid samples can be detected via laboratory analysis using United States Environmental Protection Agency analytical methodologies, and according to industry standard quality assurance and quality control requirements. Exemplary contaminant detection limits and associated sample volumes/masses necessary to meet targeted levels of detection are described in Table 1.

and transport thousands of gallons of liquid sample; and (7) the system provides efficient waste elimination, since the elutriate is immediately returned to the source.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary. Further, the terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

TABLE 1

| Contaminant Group | Liquid Sample Detection Limits | Liquid Sample Volume Required (liters) | Particulate Sample Detection Limits | Particulate Sample Mass Required (grams) |
| --- | --- | --- | --- | --- |
| PCDD/PCDFs | 0.5-5 picograms per liter | 10 | 0.5-5 nanograms per kilogram | 25 |
| PCB Congeners | 1-2 picograms per liter | 5 | 0.5-1 nanograms per kilogram | 25 |
| Aroclor PCBs | 1.0 micrograms per liter | 1 | 33 micrograms per kilogram | 30 |
| Organochlorine Pesticides | 16-160 picograms per liter | 2.5 | 4-40 nanograms per kilogram | 25 |
| SVOCs | 1-2 micrograms per liter | 2.5 | 170-330 micrograms per kilogram | 30 |
| SVOCs SIM | 4 nanograms per liter | 2.5 | 3.3 micrograms per kilogram | 30 |
| Chlorinated Herbicides | 0.2-2 micrograms per liter | 1 | 100-240 micrograms per kilogram | 50 |
| Cyanide | 10 micrograms per liter | 0.25 | 0.5 milligrams per kilogram | 5 |
| VOCs | 0.5 micrograms per liter | 0.04 | 5 micrograms per kilogram | 5 |
| TEPH | 0.30 milligrams per liter | 1 | 20 milligrams per kilogram | 30 |
| TOC | 1 microgram per liter | 0.25 | 500 milligrams per kilogram | 10 |

The mobile sample collection system described herein has several advantages over conventional methodologies for liquid sample monitoring: (1) because the system can process large volumes of liquid, greatly enhanced trace contaminant detection may be achieved with respect to dissolved solids and suspended particulate solid fractions from whole water sources; (2) the high processing capacity enables collection of targeted solids in compliance with stringent laboratory quality assurance and quality control requirements; (3) the system can accommodate U.S. EPA specifications for sample collection and analysis; (4) the "clean room" environment described herein reduces cross-contamination and simplifies decontamination; (5) direct measurement of both particulate phase and dissolved phase contaminant concentrations at trace levels allows comparison of like contaminants present in whole water samples but associated with different matrices (solids versus liquid); (6) the mobile nature of the system eliminates the need to collect

What is claimed is:

1. A mobile sample collection system comprising a housing enclosing:
   a main influent peristaltic pump operatively connected to a main tubing line;
   a continuous flow centrifuge (CFC) operatively connected to the main tubing line, the CFC comprising a centrifuge bowl; and
   an elutriate collection tank receiving elutriate from the CFC, the elutriate collection tank comprising a tank liner configured to prevent direct contact of pumped fluids with the tank,
   wherein the main influent peristaltic pump is configured to continuously pump fluids from a liquid source through the main tubing line and into the CFC, the fluids comprising suspended solids and dissolved solids, wherein the main tubing line comprises one or more sampling ports connectively linked to one or more peristaltic sampling pumps, wherein the fluids are processed through the CFC so that that the suspended solids are retained on the centrifuge bowl and so that a portion of the dissolved solids exit from the CFC through the main tubing line and are collected in the elutriate collection tank for analysis, and wherein another portion of the dissolved fluids are returned to the liquid source.

2. The system of claim 1, wherein the housing comprises a climate-controlled trailer.

3. The system of claim 1, wherein the main tubing line is operatively linked to a flow meter.

4. The system of claim 1, further comprising a sampling port connectively linking the main tubing line to a secondary tubing line operatively linked to a first peristaltic sampling pump configured to pump fluid containing dissolved solids from the CFC into the elutriate collection tank for sample collection and analysis.

5. The system of claim 1, further comprising a sampling port connectively linking the main tubing line to a secondary tubing line operatively linked to a second sampling pump configured to pump the fluids containing suspended and dissolved solids from the liquid source into a bulk liquid collection tank for sample collection and analysis.

6. The system of claim 1, further comprising a sampling port connectively linking the main tubing line to a secondary tubing line operatively linked to a third sampling pump configured to pump the fluids from the liquid source as samples for direct analysis and real-time quality monitoring.

7. The system of claim 1, further comprising:
a first sampling port connectively linking the main tubing line to a secondary tubing line operatively linked to a first peristaltic sampling pump configured to pump fluid containing dissolved solids from the CFC into the elutriate collection tank for sample collection and analysis;
a second sampling port connectively linking the main tubing line to a secondary tubing line operatively linked to a second sampling pump configured to pump the fluids from the liquid source into a bulk liquid collection tank for sample collection and analysis; and
a third sampling port connectively linking the main tubing line to a secondary tubing line operatively linked to a third sampling pump configured to pump the fluids from the liquid source as samples for direct analysis and real-time quality monitoring.

8. The system of claim 1, wherein the main peristaltic pump is capable of pumping fluids through the system at a flow rate of at least 15 gallons per minute.

9. A method for assembling the mobile sample collection system of claim 1, comprising:
providing a main influent peristaltic pump, a main tubing line, an elutriate collection tank and a CFC comprising a centrifuge bowl;
operatively configuring the main influent peristaltic pump to continuously pump fluids from a liquid source through the main tubing line, into the CFC and back to the liquid source;
operatively connecting the elutriate collection tank to the CFC so as to enable fluid containing dissolved solids to exit from the CFC through the main tubing line for collection in the elutriate collection tank, and
operatively connecting one or more sampling ports to the main tubing line and to one or more peristaltic sampling pumps.

10. The method of claim 9, comprising connectively linking a sampling port between the main tubing line and a secondary tubing line operatively linked to a first peristaltic sampling pump configured to pump elutriate fluid comprising dissolved solids from the CFC into the elutriate collection tank.

11. The method of claim 9, comprising connectively linking a sampling port between the main tubing line and a secondary tubing line operatively linked to a second peristaltic sampling pump configured to pump the fluids comprising suspended solids and dissolved solids from the liquid source into a bulk liquid collection tank.

12. The method of claim 9, comprising connectively linking a sampling port between the main tubing line and a secondary tubing line operatively linked to a third peristaltic sampling pump configured to pump the fluids from the liquid source as samples for direct analysis and real-time quality monitoring.

13. The method of claim 9, further comprising:
connectively linking a first sampling port between the main tubing line and a secondary tubing line operatively linked to a first peristaltic sampling pump configured to pump fluid comprising dissolved solids from the CFC into the elutriate collection tank;
connectively linking a second sampling port between the main tubing line and a secondary tubing line operatively linked to a second peristaltic sampling pump configured to pump the fluids comprising suspended solids and dissolved solids from the liquid source into a bulk liquid collection tank for sample collection and analysis; and
connectively linking a third sampling port between the main tubing line and a secondary tubing line operatively linked to a third peristaltic sampling pump configured to pump the fluids from the liquid source as samples for analysis and real-time quality monitoring.

* * * * *